(12) United States Patent
Tanaka et al.

(10) Patent No.: US 7,947,669 B2
(45) Date of Patent: *May 24, 2011

(54) AGENT FOR IMPROVING INSULIN RESISTANCE

(75) Inventors: Miyuki Tanaka, Zama (JP); Eriko Misawa, Zama (JP)

(73) Assignee: Morinaga Milk Industry Co., Ltd., Minato-ku, Tokyo (JP)

( * ) Notice: Subject to any disclaimer, the term of this patent is extended or adjusted under 35 U.S.C. 154(b) by 434 days.

This patent is subject to a terminal disclaimer.

(21) Appl. No.: 12/064,607

(22) PCT Filed: Sep. 22, 2006

(86) PCT No.: PCT/JP2006/318813
§ 371 (c)(1),
(2), (4) Date: Feb. 22, 2008

(87) PCT Pub. No.: WO2007/043305
PCT Pub. Date: Apr. 19, 2007

(65) Prior Publication Data
US 2010/0035851 A1   Feb. 11, 2010

(30) Foreign Application Priority Data

Sep. 30, 2005 (JP) ................. 2005-287885

(51) Int. Cl.
*A61K 31/56* (2006.01)
*A61K 33/00* (2006.01)
(52) U.S. Cl. .................. 514/178; 514/179; 424/724
(58) Field of Classification Search .................. 514/178, 514/179, 866; 424/724
See application file for complete search history.

(56) References Cited

U.S. PATENT DOCUMENTS

| | | | |
|---|---|---|---|
| 4,598,069 A | 7/1986 | Hikino et al. | |
| 7,531,520 B2 | 5/2009 | Tanaka et al. | |
| 7,534,770 B2 | 5/2009 | Higuchi et al. | |
| 2003/0207818 A1 | 11/2003 | Jia et al. | |

FOREIGN PATENT DOCUMENTS

| | | |
|---|---|---|
| JP | 59-027824 | 2/1984 |
| JP | 60-214741 | 10/1985 |
| JP | 07-165587 | 6/1995 |
| JP | 08-012573 | 1/1996 |
| JP | 08-208495 | 8/1996 |
| JP | 10-036283 | 2/1998 |
| JP | 10-298100 | 11/1998 |
| JP | 11-193296 | 7/1999 |
| JP | 2000-319190 | 11/2000 |
| JP | 2001-240544 | 9/2001 |
| JP | 2001-247473 | 9/2001 |
| JP | 2002-193797 | 7/2002 |
| JP | 2003-286185 | 10/2003 |
| JP | 2005-068132 | 3/2005 |
| WO | WO 03/063894 | 8/2003 |
| WO | WO 2005/094838 | 10/2005 |
| WO | WO 2005/095436 | 10/2005 |
| WO | WO 2006/035525 | 4/2006 |

OTHER PUBLICATIONS

Okyar et al., Effect of Aloe vera Leaves on Blood Glucose Level in Type I and Type II Diabetic Rat Models, Phytotherapy Research, vol. 15, No. 2, pp. 157-161 (2006).*
Abou Zeid, "Chemical and Biological Study of the Leaves of Some *Musa* Species," *Egypt. J. Pharm. Sci*, vol. 39, Nos. 4-6, pp. 379-398, 1998.
Okyar, et al. "Effect of *Aloe vera* Leaves on Blood Glucose Level in Type I and Type II Diabetic Rat Models," *Phytotherapy Research*, vol. 15, No. 2, pp. 157-161, 2001.
Rajasekaran, et al. "Hypoglycemic Effect of *Aloe vera* Gel on Streptozotocin-Induced Diabetes in Experimental Rats," *Journal of Medicinal Food*, vol. 7, No. 1, pp. 61-66, 2004.
Tanaka, et al. "Identification of Five Phytosterols from Aloe Vera Gel as Anti-Diabetic Compounds," *Biol. Pharm. Bull.*, vol. 29, No. 7, pp. 1418-1422, Jul. 2006.
Yeh, et al. "Systematic Review of Herbs and Dietary Supplements for Glycemic Control in Diabetes," *Diabetes Care*, vol. 26, No. 4, pp. 1277-1294, Apr. 2003.
Yongchaiyudha, et al. "Antidiabetic Activity of *Aloe vera* L. Juice. I. Clinical Trial in New Cases of Diabetes Mellitus," *Phytomedicine*, vol. 3, No. 3, pp. 241-243, 1996.
International Search Report dated Dec. 26, 2006.
Office Action issued on Feb. 12, 2010 by the State Intellectual Property Office, P.R. China to related Chinese application No. 200680036515.0.
Shimamoto, et al. "Insulin Resistance and Adult Disease—Hypertension, Diabetes, Hyperlipidemia and Obesity," pp. 1-5, 2003.
Maeda, et al. Basic "Adiponectine," *Adiposcience*, vol. 1, No. 3, pp. 247-257, 2004.
Sartipy, et al. "Monocyte Chemoattractant Protein 1 in Obesity and Insulin Resistance," *Proceedings of the National Academy of Science*, vol. 100, No. 12, pp. 7265-7270, Jun. 10, 2003.
Uysal, et al. "Protection from Obesity-Induced Insulin Resistance in Mice Lacking TNF-α Function," *Nature*, vol. 389, pp. 610-614, Oct. 9, 1997.
Jazet, et al. "Adipose Tissue as an Endocrine Organ: Impact on Insulin Resistance," *The Netherlands Journal of Medicine*, vol. 61, No. 6, pp. 194-212, Jun. 2003.
Konno, et al. "Effect of 5-campestenone (24-methylcholest-5-en-3-one) on Zucker Diabetic Fatty Rats as a Type 2 Diabetes Mellitus Model," *Hormone Metabolism Research*, vol. 37, pp. 79-83, 2005.

* cited by examiner

*Primary Examiner* — Kevin Weddington
(74) *Attorney, Agent, or Firm* — Knobbe, Martens, Olson & Bear, LLP

(57) ABSTRACT

To inhibit production of adipocytokines, in particular, adipocytokines that elicit insulin resistance and to prevent onset of pathosis caused by the insulin resistance, or improve the pathosis, the present invention provides an agent or a food or drink which contains a compound having a cyclolanostane skeleton, or an organic solvent extract, a hot water extract of a plant of the family Liliaceae or Gramineae, or a fraction thereof which contains the compound as an active ingredient.

2 Claims, 1 Drawing Sheet

AGENT FOR IMPROVING INSULIN RESISTANCE

CROSS-REFERENCE TO RELATED APPLICATIONS

This application is the U.S. National Phase under 35 U.S.C. §371 of International Application PCT/JP2006/318813, filed Sep. 22, 2006, which was published in a non-English language, which claims priority to JP Application No. 2005-287885, filed Sep. 30, 2005.

TECHNICAL FIELD

The present invention relates to an agent for improving insulin resistance, which contains a compound having a cyclolanostane skeleton as an active ingredient, and a food or drink containing the same. In particular, the present invention relates to an agent for improving insulin resistance, which has an effect of controlling production of adipocytokines that are factors involved in onset and exacerbation of pathosis in which the insulin resistance plays a role, such as free fatty acid, plasminogen activator inhibitor, tumor necrosis factor, monocyte chemoattractant protein-1 and resistin, and relates to a food or drink containing the same.

BACKGROUND ART

Insulin is a kind of hormones produced by β cells in Langerhans islets of pancreas, and plays an important role in maintaining homeostasis of living body by affecting lipid metabolism and protein metabolism as well as sugar metabolism via insulin receptors which are present in target tissues of insulin such as skeletal muscles, liver and fats. Examples of the effects of insulin in respective target tissues include promotion of absorption of glucose from blood into muscle cells and adipocytes, promotion of glycogen production in liver and muscle tissues, inhibition of gluconeogenesis in liver, promotion of glucose consumption and fatty acid synthesis in the adipocytes, and inhibition of degradation of lipids.

The insulin resistance means a state that the cells, organs or individuals require larger amounts of insulin than those typically required in order to obtain respective effects of insulin, that is, a state of impaired insulin effects where sensitivity to insulin is decreased. From results of past epidemiologic investigations, hypertension, diabetes, hyperlipidemia (hypertriglyceridemia and hypo-HDL-cholesterolemia), obesity and the like are considered insulin resistance-based pathosis. The insulin resistance causes insufficient effects of insulin in the sugar metabolism, results in compensatory hyperinsulinemia for maintaining blood sugar level, whereby hyperglycemia and glucose intolerance occur and diabetes is promoted by exhaustion of pancreatic β cells. Furthermore, the hyperinsulinemia enhances activation of sympathetic nerves and promotes sodium absorption of kidney to cause hypertension, and also induces postprandial hyperlipidemia and hyperuricemia, an increase in plasminogen activator inhibitor-1 (PAI-1), and the like.

Meanwhile, the insulin resistance induces abnormal lipid metabolism caused by the insufficient effects of insulin, and free fatty acid (FFA) released from adipocytes increases in liver to promote synthesis of triglyceride (TG), resulting in hypertriglyceridemia. Furthermore, activity of lipoprotein lipase (LPL) generally having high insulin sensitivity is decreased in the insulin resistant state, so degradation of TG is decreased and the hypertriglyceridemia is additionally exacerbated. Furthermore, with exacerbation of diabetes, complications such as retinopathy, nephropathy and gangrene caused by angiopathy occur so that cardiac infarction and cerebral infarction that are arteriosclerotic diseases exacerbate, and hypertension exacerbates cardiovascular diseases. As described above, the insulin resistance is considered to be significantly involved in exacerbation of complicated pathosis (Non-patent Document 1).

In recent years, from results of analysis of organ-specific gene expression, it was revealed that various physiologically active substances are secreted from fat tissues, and the fat tissues thus has been recognized to be not only energy storage tissues but also the largest endocrine organ in a living body. Endocrine factors derived from the fat tissues are generically called adipocytokines, and play important roles in maintenance of homeostasis in metabolism. However, it is considered that, in a case of obesity, that is, a state where fats are accumulated, an excessive or a too small amount of adipocytokines are produced and secreted, and the balance of the adipocytokines is disrupted, resulting in the insulin resistance.

The adipocytokines are classified into two groups: one that enhances insulin sensitivity; and one that elicits insulin resistance, representative examples of the former group include adiponectin, leptin, AMPK (AMP-dependent protein kinase) and the like. In particular, it has been reported that the adiponectin has an effect of canceling insulin resistance and an effect of inhibiting gluconeogenesis in liver (Non-patent Document 2).

Meanwhile, examples of the adipocytokines that elicit insulin resistance include tumor necrosis factor-α (TNF-α), monocyte chemoattractant protein-1 (MCP-1) that is a kind of inflammatory chemokine, and resistin in addition to the aforementioned FFA and PAI-1. In particular, it has been reported that TNF-α has an effect of eliciting the insulin resistance by inhibiting tyrosine phosphorylation of an insulin receptor and IRS1 (insulin receptor substrate 1) in the insulin signal transduction mechanism so that the effect of insulin is attenuated. Furthermore, it has been reported that, in the insulin resistant state, the MCP-1 level in a living body is increased and mRNA of GLUT4 (glucose transporter-4) that is a glucose-transporting carrier, PPARγ (peroxisome proliferator-activated receptor γ) that is an intranuclear receptor, β3AR (β3-adrenergic receptor) that is a kind of β type catecholamine receptor of an adipocyte, and aP2 (adipocyte fatty-acid-binding protein 2) that is a fatty-acid-binding protein are reduced. Therefore, MCP-1 is considered to be a causative agent of decreasing insulin sensitivity (Non-patent Documents 3, 4 and 5).

As agents for improving insulin resistance, biguanide agents that inhibit gluconeogenesis mainly in liver, and thiazolidine derivatives that improve the insulin sensitivity of muscles and fat tissues have been developed. Those agents have already been permitted as diabetic medicines, and also used for treatment of arteriosclerosis. The thiazolidine derivatives as represented by troglitazone and pioglitazone are each considered to act as a ligand for peroxisome proliferator-activated receptor (PPAR) that is an intranuclear receptor-type transcription factor to promote differentiation of adipocytes, thereby improving insulin resistance.

In addition, an agent for improving insulin resistance containing adiponectin or their genes as an active ingredient (Patent Document 1), a preventive and/or therapeutic agent for diseases caused by insulin resistance containing a substance having affinity to bombesin receptor subtype 3 (BRS-3) as an active ingredient (Patent Document 2), a free fatty acid (FFA) decreasing agent containing a pyrrole derivative as an active ingredient (Patent Document 3) and the like have been disclosed as the agents for improving insulin resistance. Furthermore, a composition for improving insulin resistance containing acetic acid and an ion or salt thereof as an active ingredient (Patent Document 4), an agent for improving insulin resistance comprising a fatty oil containing particular diglyceride and/or monoglyceride (Patent Document 5) and the like have been disclosed as the agents containing a substance derived from a food or drink as an active ingredient.

Plant sterols such as β-sitosterol, campesterol and stigmasterol have been known to have a decreasing effect on blood cholesterol by inhibition of absorption of cholesterol, and practical use thereof has been attempted by adding them as a fat composition to edible oil. Furthermore, an anti-obesity agent and a lipid metabolism-improving agent containing a cholestenone compound as an active ingredient which is synthesized by using plant sterols such as β-sitosterol and campesterol as a starting material have been disclosed (Patent Documents 6 to 8, and Non-patent Document 6).

Furthermore, an adiponectin secretion promoter containing an extract from at least one of rice bran, shimeji mushroom, chrysanthemum, rye, white birch and Spanish Jasmine (*Alpinia zeumber*), and cycloartane type triterpene or cycloartenol and/or (24S)-24,25-dihydroxycycloartanol which are derivatives of cycloartane type triterpene have been disclosed (Patent Document 9).

The genus *Aloe* belonging to liliaceae plant is a group of plants including *Aloe vera* (*Aloe barbadenisis* Miller), *Aloe arborescens* (*Aloe arborescens* Miller var. *natalensis* Berger) and the like, and they are empirically known to have various efficacies. For example, immunosuppression improving agents containing a butanol fraction of an aloe extract or aloin (Patent Document 10), an agent related to improving blood glucose levels (Patent Documents 11 to 14), a preventive and improving agent for obesity (Patent Document 15) and the like are disclosed, but the improving effect on insulin resistance of the plants belonging to the genus *Aloe* has not been reported.

[Patent Document 1] International Publication NO. WO2003/63894 pamphlet
[Patent Document 2] Japanese Patent Laid-open NO. 10-298100
[Patent Document 3] Japanese Patent Laid-open NO. 08-12573
[Patent Document 4] Japanese Patent Laid-open NO. 2002-193797
[Patent Document 5] Japanese Patent Laid-open NO. 2001-247473
[Patent Document 6] Japanese Patent Laid-open NO. 07-165587
[Patent Document 7] Japanese Patent Laid-open NO. 11-193296
[Patent Document 8] Japanese Patent Laid-open NO. 2001-240544
[Patent Document 9] Japanese Patent Laid-open NO. 2005-68132
[Patent Document 10] Japanese Patent Laid-open NO. 08-208495
[Patent Document 11] Japanese Patent Laid-open NO. 59-214741
[Patent Document 12] Japanese Patent Laid-open NO. 2003-286185
[Patent Document 13] U.S. Pat. No. 4,598,069
[Patent Document 14] U.S. Patent Application Publication No. 2003/0207818
[Patent Document 15] Japanese Patent Laid-open NO. 2000-319190

[Non-patent Document 1] Insulin resistance and lifestyle-related diseases, Ed. Kazuaki Shimamoto, Shindan to Chiryosha, 2003, pp. 1-5
[Non-patent Document 2] Adiposcience, vol. 1, NO. 3, 2004, pp. 247-b 257
[Non-patent Document 3] Proceedings of the National Academy of Sciences, vol. 100, 2003, pp. 7265-7270
[Non-patent Document 4] Nature, vol. 389, 1997, pp. 610-614
[Non-patent Document 5] The Netherlands Journal of Medicine, vol. 6, NO. 6, 2003, pp. 194-212
[Non-patent Document 6] Hormone Metabolism Research, vol. 37, 2005, pp. 79-83

DISCLOSURE OF THE INVENTION

With use of the biguanide agent that is a conventional agent for improving insulin resistance, gastrointestinal dysfunction or rarely lactic acidosis may occur. Furthermore, a thiazolidine derivative that is the same kind of the agent may sometimes cause severe side effects such as fluid retention, increase in body weight and liver dysfunction, so use thereof requires additional attention. Further, for the insulin resistance in states other than diabetes or hyperglycemia, it has been practically difficult to use antidiabetic agents. Under such circumstances, a development of a functional material which is excellent in safety, can be ingested on a daily basis, and can efficiently improve insulin resistance with as little a pain as possible has been desired.

In view of the aforementioned problems, the inventors of the present invention have studied mechanisms of lifestyle-related disease caused by the insulin resistance, such as hypertension, diabetes, hyperlipidemia (hypertriglyceridemia and hypo-HDL-cholesterolemia) and obesity, and have studied an agent relating to prevention, improvement and the like of the lifestyle-related diseases, that is, an agent for improving insulin resistance. The inventors of the present invention made attention to adipocytokines that are factors involved in onset and exacerbation of the insulin resistance, and assiduously studied a novel functional material capable of improving insulin resistance by controlling the aforementioned factors. As a result, the inventors of the present invention found that compounds having a cyclolanostane skeleton had an effect for controlling production of adipocytokines such as free fatty acid, TNF-α, and MCP-1 in particular, an efficient effect for decreasing production of adipocytokines that elicits the insulin resistance, thereby the insulin resistance is improved.

Regarding the aforementioned effects of the present invention, Patent Document 9 described only preventive effect of the plant extract on differentiation of cultured adipocytes, a synthesis route of a cycloartane type triterpene derivative and a promotion effect of ergosterol on secretion of adiponectin, and did not describe a promotion effect of the cycloartane type triterpene or cycloartenol that is a derivative thereof on secretion of adiponectin. In addition, it did not describe and disclose that the improving effect of the active ingredient of the present invention on insulin resistance at all.

In addition, the inventors of the present invention found that the compound having a cyclolanostane skeleton directly improve the insulin resistance without intervention of insulin secretion property or the like, by investigating using an insulin tolerance test (insulin stress test), in addition to the glucose clamp method, the steady state plasma glucose (SSPG) method and the minimal model method which are conventional methods of evaluating the insulin resistance.

Such an insulin tolerance test is not performed in the aforementioned Patent Documents 1 to 5. The inventors of the present invention found a more advantageous effect for improving insulin resistance, without being affected by insulin secretion property, than conventional effects for improving insulin resistance, and accomplished the present invention.

An object of the present invention is to provide an agent for improving insulin resistance, which contains a compound having the cyclolanostane skeleton as an active ingredient. In addition, another object of the present invention is to provide a physiologically functional food or drink containing the agent for improving insulin resistance, such as a food for specified health use.

First invention of the present application to solve the aforementioned problems is an agent for improving insulin resistance containing a compound represented by the following general formula (1) as an active ingredient.

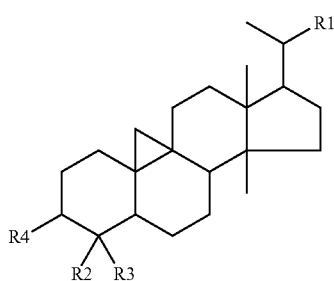
(1)

(In the formula, R1 represents an alkyl group, or an alkenyl group containing 1 or 2 double bonds or a substituted alkyl or alkenyl group containing 1 or 2 hydroxyl group and/or carbonyl group, which is straight or branched chain having 6 to 8 carbon atoms, R2 and R3 each independently represent a hydrogen atom or a methyl group, and R4 forms C=O with a carbon atom constituting the ring or is a group represented by any one of the following formulas.)

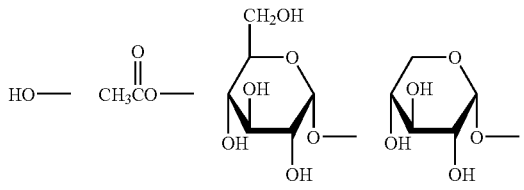

In addition, the following (1) to (3) are preferred embodiments of the present invention.
1) The aforementioned R1 is represented by any one of the following formulas, the aforementioned R2 and R3 both are methyl groups, and the aforementioned R4 is a hydroxyl group.

—CH$_2$—CH$_2$—CH$_2$—CH(CH$_3$)$_2$

—CH$_2$—CH$_2$—CHRa—C(CH$_3$)$_2$Rb (wherein Ra is any of hydrogen atom, hydroxyl or methyl group, and Rb is hydrogen atom or hydroxyl group)

—CH$_2$—CH$_2$—CH(CH$_2$CH$_3$)—CH(CH$_3$)$_2$

—CH$_2$—CH$_2$—CHRc-C(CH$_3$)=CH$_2$ (wherein Rc is any of hydrogen atom, hydroxyl or methyl group)

—CH$_2$—CH$_2$—C(=O)—C(CH$_3$)=CH$_2$

—CH$_2$—CH$_2$—C(=CH$_2$)—CH(CH$_3$)$_2$

—CH$_2$—CH$_2$—CH=C(CH$_3$)$_2$

—CH$_2$—CH=C(CH$_3$)—CH(CH$_3$)$_2$

—CH$_2$—CH$_2$—C(=CHCH$_3$)—CH(CH$_3$)$_2$

2) The aforementioned compound according to 1) is 9,19-cyclolanostan-3-ol or 24-methylen-9,19-cyclolanostan-3-ol.
3) The aforementioned compound according to 1) or 2) is contained at least 0.001% by mass.

Second invention of the present application to solve the aforementioned problems is an agent for improving insulin resistance, which contains an organic solvent extract or hot water extract of a plant containing a compound represented by the following general formula (1), or a fraction thereof as an active ingredient, wherein the organic solvent extract or hot water extract of a plant or the fraction thereof contains at least 0.001% by dry mass of a compound represented by the following general formula (1).

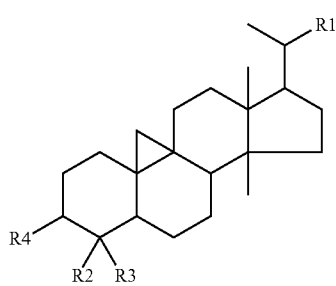
(1)

(In the formula, R1 represents an alkyl group, or an alkenyl group containing 1 or 2 double bonds or a substituted alkyl or alkenyl group containing 1 or 2 hydroxyl group and/or carbonyl group, which is straight or branched chain having 6 to 8 carbon atoms, R2 and R3 each independently represent a hydrogen atom or a methyl group, and R4 forms C=O with a carbon atom constituting the ring or is a group represented by any one of the following formulas.)

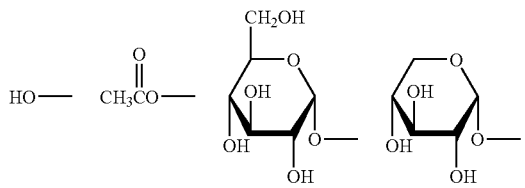

Furthermore, the following 4) to 6) are preferred embodiments of the present invention.
4) The aforementioned plant is a Liliaceae or a Gramineae plant.
5) The aforementioned R1 is represented by any one of the following formulas, the aforementioned R2 and R3 both are methyl groups, and the aforementioned R4 is a hydroxyl group.

—CH$_2$—CH$_2$—CH$_2$—CH(CH$_3$)$_2$

—CH$_2$—CH$_2$—CHRa—C(CH$_3$)$_2$Rb (wherein Ra is any of hydrogen atom, hydroxyl or methyl group, and Rb is hydrogen atom or hydroxyl group)

—CH₂—CH₂—CH(CH₂CH₃)—CH(CH₃)₂

—CH₂—CH₂—CHRc-C(CH₃)=CH₂

(wherein Rc is any of hydrogen atom, hydroxyl or methyl group)

—CH₂—CH₂—C(=O)—C(CH₃)=CH₂

—CH₂—CH₂—C(=CH₂)—CH(CH₃)₂

—CH₂—CH₂—CH=C(CH₃)₂

—CH₂—CH=C(CH₃)—CH(CH₃)₂

—CH₂—CH₂—C(=CHCH₃)—CH(CH₃)₂

6) The aforementioned compound according to 5) is 9,19-cyclolanostan-3-ol or 24-methylen-9,19-cyclolanostan-3-ol.

Third invention of the present application to solve the aforementioned problems is a food or drink containing the agent for improving insulin resistance according to the first or second invention.

In addition, the following 7) is a preferred embodiment of the present invention.

7) The food or drink contains 0.0001% by dry mass or more of the compound represented by the aforementioned general formula (1).

Fourth invention of the present application to solve the aforementioned problems is a use of a compound represented by the aforementioned general formula (1), or an organic solvent extract or hot water extract of a plant containing at least 0.001% by dry mass of the compound, or a fraction thereof, in the production of an agent for improving insulin resistance.

Fifth invention of the present application to solve the aforementioned problems is a method for improving insulin resistance, which comprises administering a compound represented by the aforementioned general formula (1), or an organic solvent extract or hot water extract of a plant containing at least 0.001% by dry mass of the compounds, or a fraction thereof, to a subject whose insulin resistance is to be improved.

In the aforementioned use and method of the present invention, a preferred embodiment of the compound represented by the aforementioned general formula (1) is the same as that of the second invention of the present invention.

The agent for improving insulin resistance of the present invention and the food or drink containing the same can be safely administered or ingested, and have preventive effects on lifestyle-related diseases which is considered to be caused by the insulin resistance. Furthermore, the active ingredient of the agent for improving insulin resistance of the present invention can be produced easily from a plant of the family Liliaceae such as *Aloe vera* (*Aloe barbadensis* Miller) that can be safely ingested from an experiential viewpoint for food and is readily available.

BEST MODE FOR CARRYING OUT THE INVENTION

Figure 1:
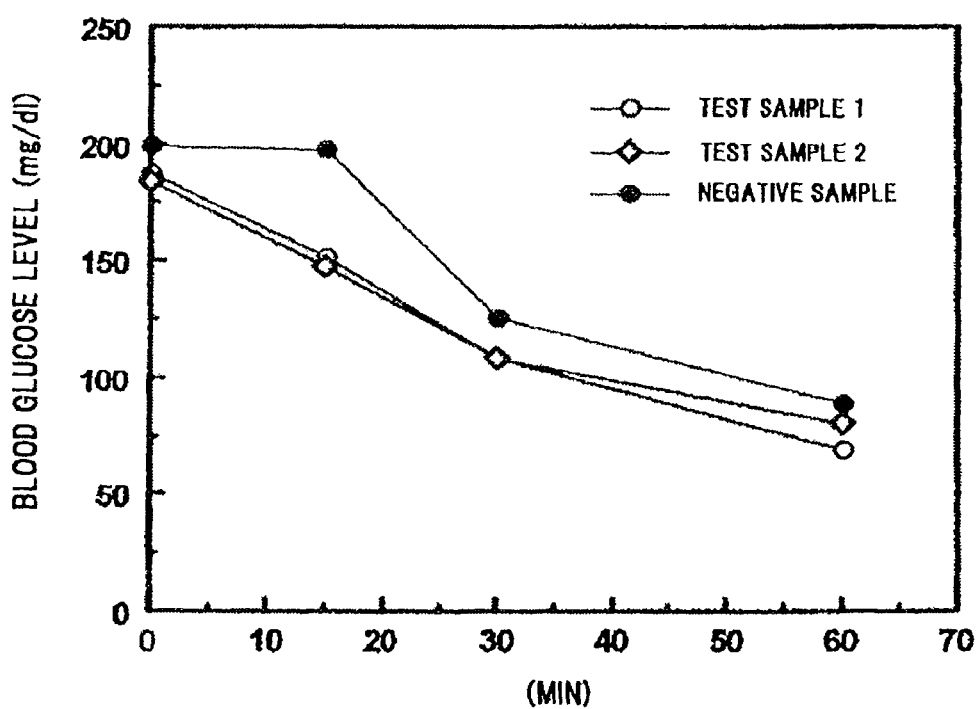
FIG. 1 is a graph showing change in blood glucose level in an insulin tolerance test.

Hereafter, preferred embodiments of the present invention will be explained in detail. However, the present invention is not limited to the following preferred embodiments and can be freely modified within the scope of the present invention. In addition, percentage as used herein indicates mass unless otherwise specified.

The compound used as the active ingredient of the agent for improving insulin resistance (hereinafter also referred to as "the agent of the present invention") of the present invention include any compounds and derivatives as long as these have the structure represented by the aforementioned general formula (1), and the effect for improving insulin resistance (hereinafter also referred to as "the compound of the present invention").

It is most preferred that a purity of the compound of the present invention used as the active ingredient of the agent for improving insulin resistance of the present invention is 100%. However, the purity can be appropriately set within a range where the agent has the effect of improving insulin resistance.

Furthermore, the composition used as the active ingredient of the agent for improving insulin resistance of the present invention (hereinafter also referred to as "the composition of the present invention") is an extract of a plant of the family Liliaceae or Gramineae, or a fraction thereof containing at least 0.001% by dry mass, preferably 0.01% by dry mass or more, and more preferably 0.1% by dry mass or more of the aforementioned compound represented by the general formula (1). The upper limit of the content of the compound of the present invention is not particularly limited, and it may be, for example, preferably 10% by mass, or 50% by mass, 70% by mass or 90% by mass.

In the present invention, dry mass means a mass measured after a compound is dried by the drying method defined by "Drying Loss Test" that is a general test method as described in Japanese Pharmacopoeia, 14th Revision (Mar. 30, 2001, the Ministry of Health, Labor and Welfare, Ministerial Notification No. 111). For example, the mass of the compound of the present invention can be determined in such a manner that: about 1 g of the compound of the present invention is measured off, and dried at 105° C. for 4 hours; and the resultant is cooled by standing in a desiccator; and the mass of the compound is weighed with scales.

According to an embodiment, the agent for improving insulin resistance of the present invention and the food or drink containing the same contain a compound having the cyclolanostane skeleton which have the effect for improving insulin resistance, as an active ingredient. The cyclolanostane skeleton is a compound represented by the following general formula (2).

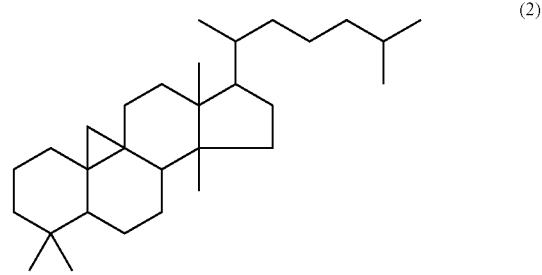

(2)

Specific examples of the compound having the cyclolanostane skeleton include compounds represented by the aforementioned general formula (1). The number of double bonds existing in the compound having the cyclolanostane skeleton is not particularly limited. Further, the number of double bonds existing in the ring is not particularly limited either. When two or more double bonds exist, they may be conjugated. The agent and food or drink of the present invention may contain two or more types of the compounds of the present invention.

In the compound of the present invention of the aforementioned general formula (1), R1 is an alkyl group or an alkenyl group containing 1 or 2 double bonds, which is straight or branched chain having 6 to 8 carbon atoms, or a substituted alkyl or alkenyl group in which one or two hydrogen atoms of the alkyl or alkenyl group are substituted by hydroxyl group and/or carbonyl group, R2 and R3 each independently are a hydrogen atom or a methyl group, and R4 forms C=O with a carbon atom constituting the ring or is a group represented by any one of the following formulas.

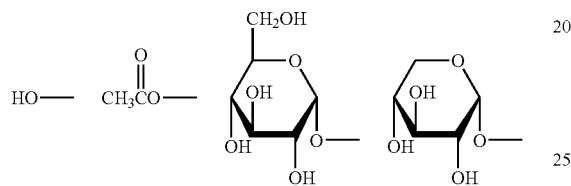

In the aforementioned general formula (1), R1 is preferably any one of the groups represented by the following formulas.

—CH$_2$—CH$_2$—CH$_2$—CH(CH$_3$)$_2$ (i)

—CH$_2$—CH$_2$—CHRa—C(CH$_3$)$_2$Rb (ii)

(wherein Ra is any of hydrogen atom, hydroxyl or methyl group, and Rb is hydrogen atom or hydroxyl group)

—CH$_2$—CH$_2$—CH(CH$_2$CH$_3$)—CH(CH$_3$)$_2$ (iii)

—CH$_2$—CH$_2$—CHRc-C(CH$_3$)=CH$_2$ (iv)

(wherein Rc is any of hydrogen atom, hydroxyl or methyl group)

—CH$_2$—CH$_2$—C(=O)—C(CH$_3$)=CH$_2$ (v)

—CH$_2$—CH$_2$—C(=CH$_2$)—CH(CH$_3$)$_2$ (vi)

—CH$_2$—CH$_2$—CH=C(CH$_3$)$_2$ (vii)

—CH$_2$—CH=C(CH$_3$)—CH(CH$_3$)$_2$ (viii)

—CH$_2$—CH$_2$—C(=CHCH$_3$)—CH(CH$_3$)$_2$ (ix)

Further, in the aforementioned general formula (1), it is preferred that R2 and R3 are both methyl groups, and the aforementioned R4 is a hydroxyl group. The most preferred compounds as the aforementioned compound are those represented by the following formulas, 9,19-cyclolanostan-3-ol (formula (3)) and 24-methylene-9,19-cyclolanostan-3-ol (formula (4))

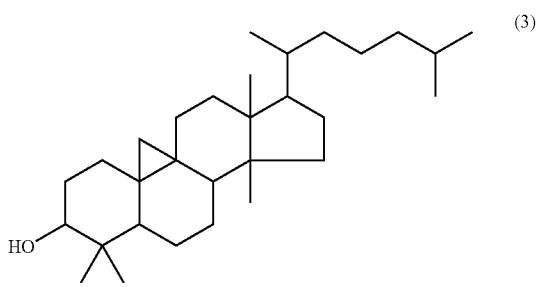

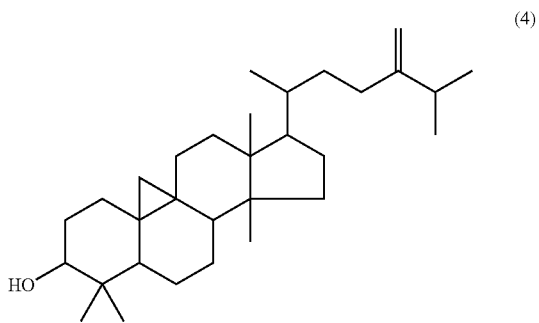

That is, 9,19-cyclolanostan-3-ol is a compound represented by the aforementioned general formula (1) wherein and R3 are methyl groups, R4 is a hydroxyl group, and R1 is a group represented by the aforementioned formula (i). Further, 24-methylene-9,19-cyclolanostan-3-ol is a compound represented by the aforementioned general formula (1) wherein R2 and R3 are methyl groups, R4 is a hydroxyl group, and R1 is a group represented by the aforementioned formula (vi).

The compound of the present invention may be cycloartenol (formula (5)) or 24-methylcycloartanol (formula (7)). Both of these compounds are compounds represented by the aforementioned general formula (1) wherein R2 and R3 are methyl groups, R4 is a hydroxyl group, and R1 is a group represented by the aforementioned formula (vii) in cycloartenol or a group represented by the aforementioned formula (ii) (Ra=CH$_3$, Rb=H) in 24-methylcycloartanol.

The compound of the present invention can be chemically produced by a known production method. For example, methods for producing cycloartenol (formula (5)) and 24-methylenecycloartanol (trivial name of 24-methylene-9,19-cyclolanostan-3-ol) (formula (4)) have been disclosed in Japanese Patent Laid-open No. 57-018617, and a method for producing cycloartenol ferulate (formula (6)) from γ-oryzanol and a method for synthesizing a compound using a hydrolysate thereof as a starting material have been disclosed in Japanese Patent Laid-open No. 2003-277269. Further, when the R1 moiety of the general formula (1) contains a double bond, various derivative compounds can be produced by using a technique of converting the double bond portion into an aldehyde by ozone decomposition reaction and binding a phosphonate to it, a technique of adding hydrogen to a double bond portion, or a technique of oxidizing the double bond portion with ozone to convert it to an aldehyde or an acid. Further, the production methods are not limited to chemical synthesis methods, and the compounds may be biologically produced by using a microorganism or the like. Alternatively, they may be produced by using enzymes derived from microorganisms.

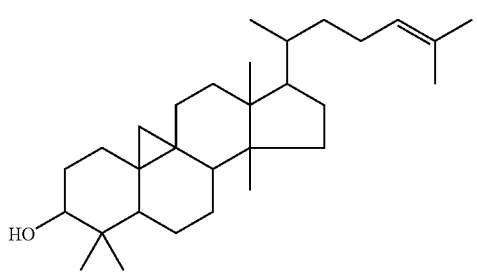

(5)

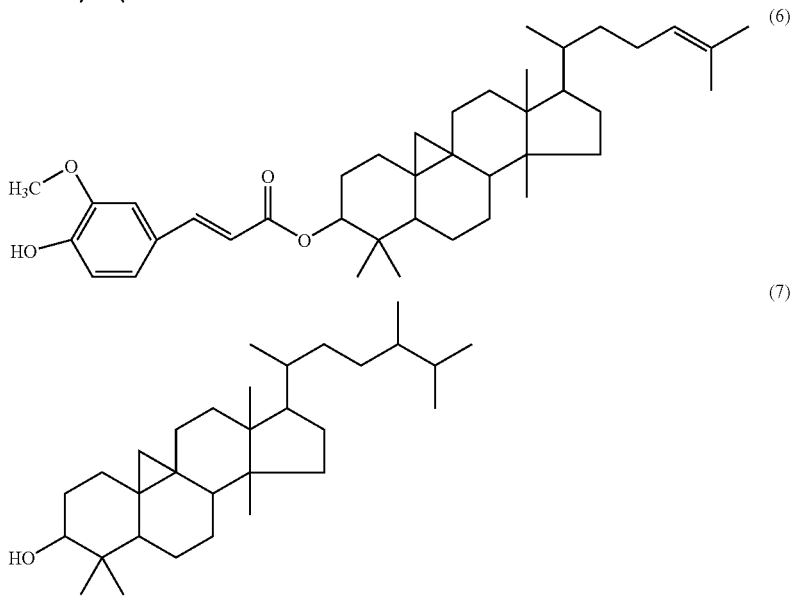

(6)

(7)

The agent for improving insulin resistance of the present invention and a food or drink containing the same may contain one type or two or more arbitrary types of the aforementioned compounds.

It is known that compounds having the cyclolanostane skeleton are contained in plants of the families Liliaceae, Leguminosae, Gramineae, Solanaceae, Musaceae and so forth (refer to Phytochemistry, U.S.A., 1977, Vol. 16, pp. 140-141; Handbook of phytochemical constituents of GRAS herbs and other economic plants, 1992, U.S.A., CRC Press; Hager's Handbuch der Pharmazeutischen Praxis, Vols. 2-6, 1969-1979, Germany, Springer-Verlag Berlin). Accordingly, the compounds can be produced by extracting from these plants, a part thereof or homogenate thereof using a method such as extraction with an organic solvent or extraction with hot water, and concentrating them.

Specifically, examples of the plant belonging to the family Liliaceae include plants belonging to the genus *Aloe* or *Allium*. Examples of the plants of the genus *Aloe* include *Aloe vera* (*Aloe barbadensis* Miller), *Aloe ferox* Miller, *Aloe africana* Miller, *Aloe arborescen* Miller var. *natalensis* Berger, *Aloe spicata* Baker and so forth. In the production of the compound of the present invention or a composition containing the same, although the whole of the aforementioned plant may be used, it is preferable to use mesophyll (clear gel portion) thereof. Such a plant or a part thereof is disrupted by using a homogenizer or the like and thereby liquefied, and the compound of the present invention or a composition containing the same is extracted from the disruption product by using an organic solvent or hot water. Examples of the organic solvent include alcohols such as methanol, ethanol and butanol; esters such as methyl acetate, ethyl acetate, propyl acetate and butyl acetate; ketones such as acetone and methyl isobutyl ketone; ethers such as diethyl ether and petroleum ether; hydrocarbons such as hexane, cyclohexane, toluene and benzene; halogenated hydrocarbons such as carbon tetrachloride, dichloromethane and chloroform; heterocyclic compounds such as pyridine; glycols such as ethylene glycol; polyhydric alcohols such as polyethylene glycol; nitrile solvents such as acetonitrile, mixtures of these solvents and so forth. Furthermore, these solvents may be anhydrous or hydrous. Among these solvents, ethyl acetate/butanol mixture (3:1) and chloroform/methanol mixture (2:1) are preferred.

As the extraction method, a method used for usual extraction of a plant component can be used. Usually used is, for example, a method of refluxing 1 to 300 parts by mass of an organic solvent with 1 part by mass of fresh plant or dried plant with heating at a temperature at or below the boiling point of the solvent and stirring or shaking, or a method of performing extraction by ultrasonication at room temperature. By isolating insoluble matters from the extraction liquor using a suitable method such as filtration or centrifugation, a crude extract can be obtained.

The crude extract can be purified by various types of chromatography such as normal or reverse phase silica gel column chromatography. When a gradient of chloroform/methanol mixture is used in normal phase silica gel column chromatography as an elution solvent, the compound of the present invention is eluted with a mixing ratio of chloroform:

methanol=about 25:1. Further, when a hexane/ethyl acetate mixture (4:1) is used in reverse phase silica gel column chromatography as an elution solvent, the compound of the present invention is eluted in a fraction eluted at an early stage. The obtained fraction can be further purified by HPLC or the like.

Further, the compound used for the present invention may also be produced by a chemical synthesis method or a biological or enzymatic method using microorganisms, enzymes or the like.

Whether the compound or composition obtained as described above actually contains the compound of the present invention can be confirmed by, for example, mass spectrometry (MS), nuclear magnetic resonance (NMR) spectroscopy or the like.

The compound of the present invention can be used as an active ingredient of the agent for improving insulin resistance of the present invention and a food or drink containing the same as it is. Further, an organic solvent extract or a hot water extract of a plant containing the compound of the present invention, or a fraction thereof (hereinafter referred to as "extract etc.") may also be used as an active ingredient of the agent for improving insulin resistance and a food or drink containing the same. In addition, when the *Aloe vera* is used as a plant of the family Liliaceae, it is preferred that total content of aloin and aloe-emodin, which are contained a lot in leaf-skin of *Aloe vera*, is 5 ppm or less.

The aforementioned extract etc. to be contained in the agent for improving insulin resistance preferably contains at least 0.001% by dry mass, more preferably 0.01 to 1% by dry mass, particularly preferably 0.05 to 1% by dry mass, of the compound of the present invention. Further, the aforementioned extract etc. to be contained in a food or drink preferably contains at least 0.0001% by dry mass, more preferably 0.001 to 1% by dry mass, particularly preferably 0.005 to 1% by dry mass, of the compound of the present invention. The aforementioned extract etc. may contain two or more types of the compound of the present invention. Further, the aforementioned extract etc. may be a solution, or can also be lyophilized or spray-dried in a conventional manner and stored or used as powder.

As the agent for improving insulin resistance of the present invention, the compound of the present invention or the composition containing the same such as extract etc. per se, or those combined with a pharmaceutically acceptable carrier can be orally or parenterally administered to a mammal including human. In the agent of the present invention, the compound of the present invention may be a pharmaceutically acceptable salt. Examples of the pharmaceutically acceptable salt include both metal salts (inorganic salts) and organic salts including, for example, those listed in "Remington's Pharmaceutical Sciences," 17th edition, p. 1418, 1985. Specific examples thereof include, but not limited to, inorganic acid salts such as hydrochloride, sulfate, phosphate, diphosphate and hydrobromate, and organic acid salts such as malate, maleate, fumarate, tartarate, succinate, citrate, acetate, lactate, methanesulfonate, p-toluenesulfonate, pamoate, salicylate and stearate. Furthermore, the salt may be a salt with a metal such as sodium, potassium, calcium, magnesium and aluminum or a salt with an amino acid such as lysine. Furthermore, solvates such as hydrates of the aforementioned compound or pharmaceutically acceptable salts thereof also fall within the scope of the present invention.

Dosage form of the agent for improving insulin resistance of the present invention is not particularly limited and can be suitably selected depending on the therapeutic purpose. Specific examples thereof include tablet, pill, powder, solution, suspension, emulsion, granules, capsule, syrup, suppository, injection, ointment, patch, eye drop, nasal drop and so forth. For the preparation, additives generally used in usual agent for improving insulin resistance as pharmaceutical carriers such as excipients, binders, disintegrating agents, lubricants, stabilizers, flavoring agents, diluents, surfactants and solvents for injection and so forth can be used. Further, so long as the effect of the present invention is not degraded, the compound of the present invention, or the extract etc. containing the same can be used in combination with other agents having an effect for improving insulin resistance.

Although the amount of the compound of the present invention or the extract etc. containing the same contained in the agent for improving insulin resistance of the present invention is not particularly limited and can be suitably selected, the amount may be, for example, at least 0.001% by mass, preferably 0.01 to 1% by mass, particularly preferably 0.05 to 1% by mass, in terms of the amount of the compound of the present invention.

In the present invention, the effect of improving insulin resistance (the effect of enhancing insulin sensitivity) means an effect for preventing or improving various adverse effects on health caused by a decrease in insulin sensitivity, such as lifestyle-related diseases. Specifically, the agent of the present invention efficiently inhibits an increase or production of adipocytokines that elicit insulin resistance, such as plasminogen activator inhibitor (PAI-1), free fatty acid (FFA), tumor necrosis factor (TNF-$\alpha$), MCP-1 and resistin, and has an effect on decreasing risks, prevention, improvement or treatment of the diseases involved in the insulin resistance. Thus, the agent for improving insulin resistance of the present invention can be defined as an agent for enhancing insulin sensitivity or an agent for controlling adipocytokines production, in particular, an agent for controlling production of an adipocytokines that elicits insulin resistance.

There are methods for evaluating insulin resistance such as the glucose clamp test, the steady state plasma glucose (SSPG) method, the minimal model method, a method of evaluating the insulin resistance by calculating homeostasis model assessment insulin resistance (HOMA-IR) from fasting blood glucose level and blood insulin concentration, and the insulin tolerance test. Any of the aforementioned methods can be used for the evaluation of the insulin resistance, however, in the present invention, it is preferred to use the insulin tolerance test using animals, because the test does not affected by insulin secretion property or the like, and thus the insulin sensitivity can be directly investigated.

The compound of the present invention has an effect of increasing insulin sensitivity, and thus can prevent or improve pathosis caused by insulin resistance. Therefore, the compound can be used as an active ingredient of the agent for improving insulin resistance or a food or drink containing the same. In addition, the insulin sensitivity can also be evaluated by measuring a decrease in blood glucose level after administration of insulin.

The agent for improving insulin resistance of the present invention can prevent, improve or treat various diseases, complications and the like caused by insulin resistance, and can decrease the risks of those diseases, complications and the like. Furthermore, the agent for improving insulin resistance of the present invention can preferably be used for a patient whose insulin resistance is more aggravated than that of a healthy person In addition, insulin resistance generally means a state where a fasting plasma insulin level is 10 to 15 µU/ml or more, and a HOMA index is 1.73 or more.

Examples of the various diseases caused by insulin resistance include hypertension, hyperlipidemia, diabetes, abnormal glucose tolerance, arteriosclerosis, hyperinsulinemia and obesity. Examples of the complications caused by the diseases include (a) cerebral stroke, nephrosclerosis and renal failure caused by hypertension, (b) arteriosclerosis and pancreatitis caused by hyperlipidemia, (c) diabetic retinopathy, nephropathy, neuropathy and diabetic gangrene caused by diabetes, and (d) cerebral stroke, cerebral infarction, cardiovascular diseases such as angina pectoris and cardiac infarction, nephropathy such as uremia, nephrosclerosis and renal failure caused by arteriosclerosis. In addition, the inventors of the present invention have found that the compound of the present invention has an effect of decreasing hemoglobin A1c level and improving hyperglycemia (WO 2006/035525). It is preferred that the diseases to which the agent for improving insulin resistance of the present invention is applied are not accompanied with a state where the hemoglobin A1c level is higher than that of a healthy person.

Furthermore, an agent of the present invention which has an effect of improving insulin resistance is expected to have an effect of inhibiting production and increase of adipocytokines which elicit insulin resistance, such as TNF-$\alpha$, MCP-1 and FFA. Therefore, the agent of the present invention has an effect of preventing and/or improving the diseases caused by the increase of the aforementioned adipocytokines which include autoimmune diseases such as rheumatoid arthritis, Crohn's disease, inflammatory diseases in various organs such as nephritis, pancreatitis, hepatitis and pneumonitis, angiopathy, sepsis, cancer cachexia. Thus, the agent for improving insulin resistance of the present invention can preferably be used for a patient in which the production of the adipocytokines is enhanced, in particular, a patient in which the production of the adipocytokines that elicit the insulin resistance is enhanced.

The administration time of the agent of the present invention is not particularly limited and can be suitably selected according to the method for treating an objective disease. Furthermore, the administration route is preferably determined depending on the dosage form, age, sex and other conditions of patients, severity of symptoms of patients and so forth. The dose of the agent of the present invention is suitably selected depending on the dosing regimen, age, sex, severity of disease, other conditions of patients and so forth. The amount of the compound of the present invention as an active ingredient is usually selected from the range of, preferably 0.001 to 50 mg/kg/day, more preferably 0.01 to 1 mg/kg/day, as a tentative dose. Further, when an extract etc. containing the compound of the present invention is used, the dry weight of the extract etc. is selected from the range of, preferably 0.1 to 1000 mg/kg/day, more preferably 1 to 100 mg/kg/day, as a tentative amount. In any case, the dose can be ingested, in a day, once or several times as divided portions.

The compound of the present invention or the composition containing the same can be added to food or drink (a drink or a food) to produce a food or drink having an effect of improving insulin resistance. The form and property of the food or drink are not particularly limited so long as the effect of the active ingredient is not degraded, and the food or drink can be orally ingested, and it can be produced in a conventional manner by using raw materials usually used for food or drink except that the aforementioned active ingredient is added. Furthermore, the amount of the compound of the present invention or the extract etc. containing the same contained in the food or drink of the present invention is not particularly limited and can be suitably selected. For example, the compound of the present invention or the extract etc. containing the same is contained in food or drink in an amount of at least 0.0001% by mass, preferably 0.001 to 1% by mass, more preferably 0.005 to 1% by mass, in terms of the amount of the compound of the present invention.

The food or drink of the present invention can be used for various applications utilizing the effect of improving insulin resistance. For example, it can be used as food or drink useful for decreasing or eliminating risk factors of lifestyle-related diseases caused by insulin resistance. Furthermore, the food or drink of the present invention can prevent the diseases caused by insulin resistance, for example, hypertension, hyperlipidemia, diabetes and the like and can decrease risks of these diseases. Furthermore, the food or drink of the present invention can prevent various complications caused by insulin resistance, for example, cerebral stroke, nephrosclerosis and renal failure caused by hypertension, arteriosclerosis, pancreatitis and the like caused by hyperlipidemia, diabetic retinopathy, nephropathy, neuropathy and diabetic gangrene caused by diabetes, cerebral stroke, cerebral infarction, cardiovascular diseases such as angina pectoris and cardiac infarction, nephropathy such as uremia, nephrosclerosis and renal failure caused by arteriosclerosis, and can decrease risks of these diseases.

Furthermore, the food or drink of the present invention is expected to have an effect of inhibiting production and increase of adipocytokines that elicit insulin resistance, such as TNF-$\alpha$, MCP-1 and FFA. Therefore, the agent of the present invention has an effect of preventing the diseases and decreasing risks of these diseases caused by the increase of the aforementioned adipocytokines which include autoimmune diseases such as rheumatoid arthritis, Crohn's disease, inflammatory diseases in various organs such as nephritis, pancreatitis, hepatitis and pneumonitis, angiopathy, sepsis, cancer cachexia. Thus, the food or drink of the present invention can preferably be ingested by a patient in which the production of the aforementioned adipocytokines is enhanced, in particular, a patient in which the production of the adipocytokines that elicit insulin resistance is enhanced.

The food or drink of the present invention is preferably marketed as food or drink attached with an indication that the food or drink is used for improving insulin resistance, for example, "food or drink containing a compound having an effect of improving insulin resistance indicated as 'For improving insulin resistance'", "food or drink containing a plant extract indicated as 'For improving insulin resistance'", or "food or drink containing *Aloe vera* extract indicated as 'For improving insulin resistance'" and the like. In addition, because the compound of the present invention, and the composition containing the same have an effect for improving insulin resistance, the indication of "improving insulin resistance" is thus considered to have a meaning of "enhancing insulin sensitivity". Therefore, the food or drink of the present invention can be indicated as "For enhancing insulin sensitivity". In other words, the indication of "For improving insulin resistance" may be replaced by the indication of "For enhancing insulin sensitivity".

The wording used for such an indication as mentioned above is not necessarily be limited to the expression "For improving insulin resistance" or "For enhancing insulin sensitivity", and any other wording expressing the effect for enhancing insulin sensitivity, or the effect for preventing and improving insulin resistance of course falls within the scope of the present invention. As such a wording, for example, an indication based on various uses allowing consumers to recognize the effect for improving insulin resistance or the effect for enhancing insulin sensitivity is also possible. Examples include indication of "Suitable for those who tend to be insulin resistance" and "Useful for decrease or elimination of risk factors (risks) of lifestyle-related diseases".

The aforementioned term "indication" includes all actions for informing consumers the aforementioned use, and any indications reminding or analogizing the aforementioned use fall within the scope of the "indication" of the present invention regardless of purpose, content, objective article, medium etc. of the indication. However, the indication is preferably made with an expression that allows consumers to directly recognize the aforementioned use. Specific examples include actions of indicating the aforementioned use on goods or packages of goods relating to the food or drink of the present invention, actions of assigning, delivering, displaying for the purpose of assigning or delivering or importing such goods or packages of goods indicated with the aforementioned use, displaying or distributing advertisements, price lists or business papers relating the goods with indicating the aforementioned use, or providing information including those as contents with indicating the aforementioned use by an electromagnetic method (Internet etc.) and so forth. The indication is preferably an indication approved by the administration etc. (for example, an indication in a form based on an approval, which is qualified on the basis of any of various legal systems provided by the administration), and it is particularly preferably an indication on advertisement materials at the sales spots such as packages, containers, catalogs, pamphlets and POPs, others documents and so forth.

Examples of the indication further include indications as health food, functional food, enteric nutritive food, food for special dietary uses, food with nutrient function claims, quasi-drug and so forth as well as indications approved by the Ministry of Health, Labor and Welfare, for example, indications approved on the basis of the system of food for specified health uses and similar systems. Examples of the latter include indications as food for specified health uses, indications as food for specified health uses with qualified health claims, indications of influence on body structures and functions, indications of reduction of disease risk claims and so forth, and more precisely, typical examples include indications as food for specified health uses (especially indications of use for health) provided in the enforcement regulations of Health Promotion Law (Japan Ministry of Health, Labor and Welfare, Ministerial ordinance No. 86, Apr. 30, 2003) and similar indications.

The present invention will be explained more specifically with reference to the following examples. However, the scope of the present invention is not limited to the following examples.

Preparation examples of compounds having the cyclolanostane skeleton will be mentioned below.

Preparation Example 1

9,19-cyclolanostan-3-ol (formula (3)), 24-methylene-9,19-cyclolanostan-3-ol (formula (4)), cycloartenol (formula (5)) and 24-methylcycloartanol (formula (7)) were prepared by the method described below.

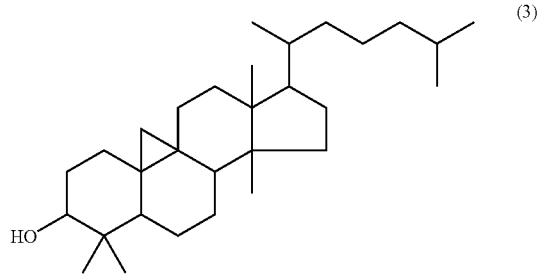

(3)

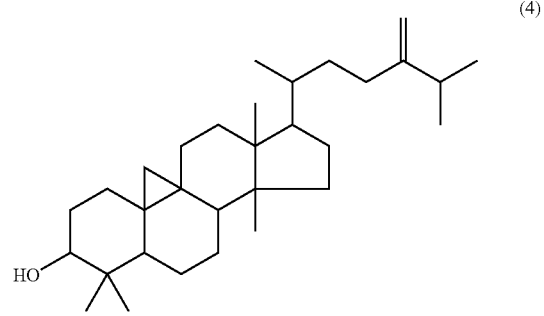

(4)

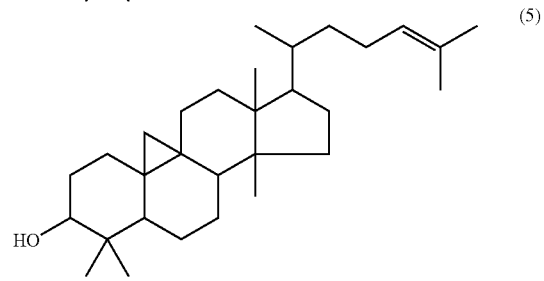

(5)

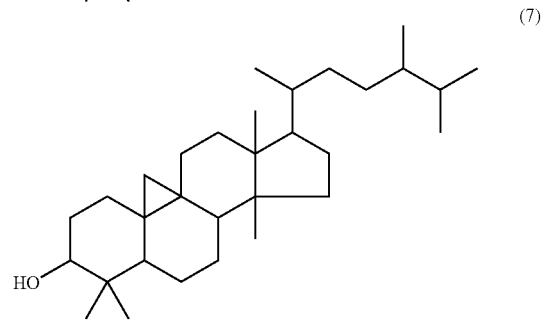

(7)

To 8.0 g of γ-oryzanol (Oryza Oil & Chemical Co., Ltd.) was added 250 ml of distilled water, 50 g of sodium hydroxide, 150 ml of isopropanol, 150 ml of ethanol and 150 ml of methanol, and the mixture was refluxed with heating for 2 hours by using a mantle heater After the reaction, the reaction mixture was poured into 1300 ml of water, and the produced white precipitates were isolated by suction filtration. To wash off the remaining alkali, the residue obtained by the filtration was suspended in 1000 ml of water, and then collected by suction filtration again. This procedure was repeated twice, and the finally obtained residue was lyophilized under reduced pressure to obtain 5.91 g of an oryzanol hydrolysate. This hydrolysate was purified by HPLC to obtain 2435 mg of 9,19-cyclolanostan-3-ol and 1543 mg of 24-methylene-9,19-cyclolanostan-3-ol.

The obtained 9,19-cyclolanostan-3-ol was used to synthesize cycloartenol. In an amount of 302 mg of 9,19-cyclolanostan-3-ol, 150 ml of isopropanol and 1.0 g of powdery 5% palladium/carbon catalyst were charged into a sealed autoclave, the internal atmosphere was replaced with a nitrogen gas, and then a hydrogen gas was introduced with applying 3 kg/cm$^2$ of pressure. The mixture was heated with stirring, and when the temperature reached 50° C., the hydrogen pressure was adjusted to 5 kg/cm$^2$. With supplementing hydrogen for the absorbed hydrogen to maintain the pressure, the reaction was allowed for 6 hours. The reaction mixture was filtered to remove the catalyst, concentrated and then purified by silica gel column chromatography (developing solvent: 100% chloroform) to obtain 275 mg of cycloartenol. 24-Methyl-cycloartanol was synthesized by using 24-methylene-9,19-cyclolanostan-3-ol as a starting material. In an amount of 78 mg of 24-methylene-9,19-cyclolanostan-3-ol, 150 ml of isopropanol and 1.0 g of powdery 5% palladium/carbon catalyst were charged into a sealed autoclave, the internal atmosphere was replaced with a nitrogen gas, and then a hydrogen gas was introduced with applying 3 kg/cm$^2$ of pressure. Then, the mixture was heated with stirring, and when the temperature reached 50° C., the hydrogen pressure was adjusted to 5 kg/cm$^2$. With supplementing hydrogen for the absorbed hydrogen to maintain the pressure of 5 kg/cm$^2$, the reaction was allowed for 6 hours. The reaction mixture was filtered to remove the catalyst, concentrated and then purified by silica gel column chromatography (developing solvent: 100% chloroform) to obtain 69 mg of 24-methylcycloartanol.

Preparation examples of extracted compositions containing a compound having the cyclolanostane skeleton using *Aloe vera* (*Aloe barbadensis* Miller) belonging to Liliaceae plant as a starting material will be described below.

Preparation Example 2

In an amount of 100 kg of hulled *Aloe vera* (*Aloe barbadensis* Miller) was liquefied by using a homogenizer, added with 100 L of an ethyl acetate ester/butanol mixture (3:1) and stirred. The mixture was left overnight to separate the ethyl acetate ester/butanol mixture and the aqueous layer, and the ethyl acetate ester/butanol mixture was recovered. The extracted composition containing a compound having the cyclolanostane skeleton, which was obtained by concentrating the ethyl acetate ester/butanol mixture under reduced pressure, weighed 13.5 g. LC-MS measurement of this composition revealed that the content of 9,19-cyclolanostan-3-ol was 10 mg, and the content of 24-methylene-9,19cyclolanostan-3-ol was 70 mg.

Preparation Example 3

In an amount of 1 kg of *Aloe vera* powder was added with 10 L of a chloroform/methanol mixture (2:1) and immersed overnight in the mixture at room temperature, and then the chloroform/methanol mixture was recovered. The organic solvents were completely removed from this mixture at 28° C. to obtain 83 g of a composition containing a compound having the cyclolanostane skeleton. LC-MS measurement of this composition revealed that the content of 9,19-cyclolanostan-3-ol was 25.8 mg, and the content of 24-methylene-9,19-cyclolanostan-3-ol was 24 mg.

Example 1

This example was performed in order to evaluate a change in the level of free fatty acid (FFA) in blood serum caused by an application of the agent of the present invention for improving insulin resistance by using AKR mice in which insulin resistance is induced by feeding with a high-fat diet.
(1) Preparation of Samples
Each of 9,19-cyclolanostan-3-ol and 24-methylene-9,19-cyclolanostan-3-ol produced in Preparation Example 3 was dissolved in DMSO, and each concentration was adjusted to 1 μg/ml with distilled water to thereby prepare Test Samples 1 and 2. In this case, the final DMSO concentration was adjusted to 0.2%. Furthermore, a solution without the test samples was prepared as a negative sample.
(2) Test Method
6-week-old male AKR mice (purchased from The Jackson Laboratory, USA) were preliminarily fed with a high-fat diet (Research Diet, Inc.) for 2 months to induce insulin resistance. These mice were divided into groups, each consisting of 8 mice. Each of the groups of mice was orally administered with 1 ml per 40 g of body weight (25 μg/kg of body weight) of the Test Samples 1, 2 or the negative sample once a day everyday with a sonde. On the 60th day from the initiation of the administration of the samples, blood was collected from the mice under fasting, and the level of the free fatty acid in serum was measured by using NEFA C-test Wako (Wako Pure Chemical Industries, Ltd.).
(3) Results (Level of Free Fatty Acid in Blood)
Table 1 shows levels of free fatty acid in mice serum at 60th day from the initiation of the administration. As compared with the group administered with the negative sample, it was observed that the free fatty acid levels tend to decrease to 81.1% in the group administered with Test Samples 1 or 2. Therefore, it was revealed that the administration of the agent for improving insulin resistance of the present invention decreases systemic level of the free fatty acid and thus exhibits a preventive effect on elicit of insulin resistance.

TABLE 1

| Sample | Free fatty acid (mEq/l) | Test Sample/Negative sample (%) |
|---|---|---|
| Test Sample 1 | 1.20 ± 0.38 | 81.1 |
| Test Sample 2 | 1.20 ± 0.25 | 81.1 |
| Negative sample | 1.48 ± 0.17 | — |

Example 2

This example was performed in order to evaluate an effect of the agent for improving insulin resistance of the present invention on production quantities of TNF-α and MCP-1 in each cell of adipose tissue by using AKR mice in which insulin resistance is induced by feeding with a high-fat diet.
(1) Preparation of Samples
In Example 2, the same Test Samples 1, 2 and the negative sample as those prepared in Example 1 were used.
(2) Test Method
6-week-old male AKR mice (purchased from The Jackson Laboratory, USA) were preliminarily fed with a high-fat diet (Research Diet, Inc.) for 2 months to induce insulin resistance. These mice were divided into groups, each consisting of 8 mice. Each of the groups of mice was orally administered with 1 ml per 40 g of body weight (25 μg/kg of body weight) of the Test Sample 1, 2 or the negative sample once a day everyday with a sonde. On the 60th day from the initiation of the administration of the samples, epididymal fats tissues were collected from the mice under fasting, and 1 g of each of the fats was added with 1.5 ml of D-MEM/F12 medium containing 0.5% bovine serum albumin, followed by culturing at 37° C. After 1 hour of the culture, culture supernatants were collected, and concentrations of TNF-α and MCP-1 in the culture supernatants were measured by ELISA method (Biosource).
(3) Results (Production Quantities of TNF-α and MCP-1)
Table 2 shows production quantities of TNF-α of adipose tissues. Table 3 shows production quantities of MCP-1 of adipose tissues. As apparent from these results, significant inhibitory effects on the production of both of TNF-α and MCP-1 was observed in the group administered with the Test Sample 1 or 2 as compared with the group administered with the negative sample. From the results of the present example, it was revealed that the administration of the agent for improving insulin resistance of the present invention decreases the production of adipocytokines in the fat tissues that exacerbate the insulin resistance, and prevent the elicit of the insulin resistance. In addition, p values in the tables indicate significance probability by Tukey-Kramer's test.

TABLE 2

| Sample | TNF-α (pg/ml) | p value |
| --- | --- | --- |
| Test Sample 1 | 29.80 ± 2.58 * | 0.0039 |
| Test Sample 2 | 33.59 ± 0.59 * | 0.0365 |
| Negative sample | 37.89 ± 2.56 | — |

In the Table, "*" indicates that there was a statistically significant inhibitory effect on TNF-α production.

TABLE 3

| Sample | MCP-1 (pg/ml) | P value |
| --- | --- | --- |
| Test Sample 1 | 89.83 ± 6.16 * | 0.0018 |
| Test Sample 2 | 99.32 ± 7.80 * | 0.0114 |
| Negative sample | 122.92 ± 10.06 | — |

In the Table, "*" indicates that there was a statistically significant inhibitory effect on MCP-1 production.

Example 3

This example was performed in order to evaluate an enhancing effect of the agent for improving insulin resistance of the present invention on insulin sensitivity by performing an insulin tolerance test using AKR mice in which insulin resistance is induced by feeding with a high-fat diet.

(1) Preparation of Samples

In Example 3, the same Test Samples 1, 2 and the negative sample as those prepared in Examples 1 and 2 were used.

(2) Test Method 6-week-old male AKR mice (purchased from The Jackson Laboratory, USA) were preliminarily fed with a high-fat diet (Research Diet, Inc.) for 2 months to induce insulin resistance. These mice were divided into groups, each consisting of 8 mice. Each of the groups of mice was orally administered with 1 ml per 40 g of body weight (25 μg/kg of body weight) of the Test Samples 1, 2 or the negative sample once a day everyday with a sonde. On the 45th day from the initiation of the administration of the samples, an insulin tolerance test was performed. In the present example, the insulin tolerance test was performed in such a manner that: the mice were fasted for 4 hours, and were then intraperitoneally administered with 0.75 U/Kg of body weight of a human insulin (Eli Lily and Company); and changes with time in blood glucose level were measured from the initiation of the administration of the insulin to after 60 minutes later.

(3) Results (Insulin Tolerance Test)

The results of the present example were as shown in FIG. 1. FIG. 1 shows the results of the insulin tolerance test. As apparent from FIG. 1, rapid decrease in blood glucose levels immediately after the initiation of the insulin was observed in the group administered with the Test Sample 1 or 2, while no decrease in blood glucose level was observed for 15 minutes after the initiation of the administration of insulin in the group administered with the negative sample. From the results of the present example, it was revealed that the administration of the agent for improving insulin resistance of the present invention enhances the insulin sensitivity.

INDUSTRIAL APPLICABILITY

The present invention can provide an agent for improving insulin resistance which is safe without side effects and is capable of enhancing insulin sensitivity, and can provide a physiologically functional food or drink such as foods for specified health use containing the agent for improving insulin resistance. The agent for improving insulin resistance and the physiologically functional food or drink containing the same of the present invention have improving or preventive effects on diseases, complications and the like caused by a decrease insulin sensitivity, for example the lifestyle-related diseases such as hypertension, diabetes, hyperlipidemia and arteriosclerosis, and have decreasing effects on risks of those diseases, complications and the like.

What is claimed is:

1. A method for treating hyperinsulinemia or abnormal glucose tolerance, which comprises administering at least 0.001% by mass of 9,19-cyclolanostan-3-ol or 24-methylen-9,19-cyclolanostan-3-ol, obtainable from an ethyl acetate/butanol mixture extract or a chloroform/methanol mixture extract of a plant of the genus *Aloe*, or a fraction thereof which comprises the compound, to a subject whose hyperinsulinemia or abnormal glucose tolerance is to be treated.

2. A method for treating hyperinsulinemia or abnormal glucose tolerance, which comprises administering at least 0.001% by mass of 9,19-cyclolanostan-3-ol or 24-methylene-9,19-cyclolanostan-3-ol, to a subject whose hyperinsulinemia or abnormal glucose tolerance is to be treated.

* * * * *